United States Patent
Behre et al.

(10) Patent No.: US 6,610,893 B2
(45) Date of Patent: Aug. 26, 2003

(54) METHOD FOR PRODUCING 4-HYDROXY-3-NITROBIPHENYL

(75) Inventors: Horst Behre, Odenthal (DE); Michael Dockner, Köln (DE); Alexander Klausener, Pulheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/240,966

(22) PCT Filed: Mar. 28, 2001

(86) PCT No.: PCT/EP01/03520
§ 371 (c)(1),
(2), (4) Date: Oct. 7, 2002

(87) PCT Pub. No.: WO01/77061
PCT Pub. Date: Oct. 18, 2001

(65) Prior Publication Data
US 2003/0055294 A1 Mar. 20, 2003

(30) Foreign Application Priority Data
Apr. 10, 2000 (DE) .......................................... 100 17 818

(51) Int. Cl.$^7$ .............................................. C07C 205/00
(52) U.S. Cl. ....................................... 568/710; 562/400
(58) Field of Search ........................... 568/710; 562/400

(56) References Cited

FOREIGN PATENT DOCUMENTS

| DE | 1 016 716 | 10/1957 |
|----|-----------|---------|
| FR | 1452911   | 9/1966  |

OTHER PUBLICATIONS

Raiford: "3–Nitro–4–Hydroxydiphenyl and some of its derivatives" J. Amer. Chem. Soc., Bd. 47, 1925, Seiten 1454–1458, XP001013036 in der Anmeldung erwähnt das ganze Dokument.

Raiford et al, J. American Chemistry Society, vol. 47, pp. 1454 to 1458, 1925.*

* cited by examiner

*Primary Examiner*—Alan L. Rotman
*Assistant Examiner*—Hector M Reyes
(74) *Attorney, Agent, or Firm*—Godfried R. Akorli; Diderico van Eyl

(57) ABSTRACT

A process is provided for preparing 4-hydroxy-3-nitrobiphenyl from 4-hydroxy-biphenyl by nitrating in the position adjacent to the phenolic hydroxyl group in high selectivity and yield, and the nitric acid used as the nitrating reagent is metered into the reaction system in a specific manner.

17 Claims, No Drawings

METHOD FOR PRODUCING 4-HYDROXY-3-NITROBIPHENYL

The present invention relates to a process for preparing 4-hydroxy-3-nitrobiphenyl from 4-hydroxybiphenyl by selectively nitrating in the position adjacent to the phenolic hydroxyl group.

4-Hydroxy-3-nitrobiphenyl is an important precursor for preparing crop protecting agents. However, there exist in the literature only very few examples for preparing 4-hydroxy-3-nitrobiphenyl. In principle, they can be divided into two groups.

Firstly, Liebigs Ann. Chem. 598, 123 (1955) and DE-A-1 016 716 disclose the photochemical assembly of 2-nitro-1,4-benzoquinone 4-diazide and benzene. However, the reaction proceeds in only a very low yield of 25%.

Secondly, 4-hydroxybiphenyl may be converted to 4-hydroxy-3-nitrobiphenyl by nitrating. Examples of nitrating reagents include silver nitrate, nitryl chloride and nitric acid.

According to J. Org. Chem. 32, 300 (1967), silver nitrate is reacted with the chloroformate of 4-hydroxybiphenyl to give the corresponding nitrocarbonate. The nitro group is then selectively introduced into the desired 3-position in a yield of 97% in a rearrangement reaction of the intermediate.

When nitryl chloride is used as the nitrating reagent, 4-hydroxy-3-nitrobiphenyl is prepared only in impure form (J. Chem. Soc. Perkin Trans. 2 1985, 2013), and the impurities are not specified. The presence of dinitro- and trinitrohydroxybiphenyl cannot be ruled out.

When nitric acid is used as the nitrating reagent, the nitrating selectivity depends very strongly on the solvent used. According to Chem. Ber. 6, 193 (1873), the reaction of 4-hydroxybiphenyl and nitric acid in an aqueous system with subsequent heating results not only in mononitrohydroxybiphenyl, but also in dinitrohydroxybiphenyl and even trinitrohydroxybiphenyl. Only by steam distillation of the reaction mixture is 4-hydroxy-3-nitrobiphenyl obtained in pure form.

FR-A-1.452.911 also describes the reaction of 4-hydroxybiphenyl with dilute nitric acid in the absence of organic solvents. When 4-hydroxybiphenyl is added to 50% nitric acid at 50° C., dinitrohydroxybiphenyl in particular is formed.

In contrast, substantially higher selectivity is obtained by nitrating in glacial acetic acid using 32% nitric acid according to J. Am. Chem. Soc. 47, 1454 (1925). The 4-hydroxybiphenyl is first dissolved in glacial acetic acid and then nitric acid is added dropwise. Only then is the reaction mixture heated. However, in order to obtain the desired selectivity, it is necessary to work with a very dilute solution of 4-hydroxybiphenyl in glacial acetic acid (1.7% by weight of 4-hydroxybiphenyl). The crude yield is reported as 80–88%, but the constraint of working at high dilution distinctly compromises the economic attractiveness of the process.

All methods described for preparing 4-hydroxy-3-nitrobiphenyl starting from 4-hydroxybiphenyl are thus unsatisfactory with regard to carrying out the process on the industrial scale, since selective introduction of the nitro group into the 3-position either dictates the use of expensive nitrating reagents or requires working at high dilution. Despite the good to very good nitrating selectivity obtained, costly and inconvenient, usually distillative, purification is additionally required.

The assembly of the biaryl system by the photochemical route from a commercially unavailable reactant succeeds only in a low yield and therefore appears to be quite unattractive.

It is accordingly an object of the present invention to provide a process by which 4-hydroxynitrobiphenyl may be prepared in a simple manner and in high yield and selectivity starting from 4-hydroxybiphenyl using inexpensive reagents.

The invention provides a process for preparing 4-hydroxy-3-nitrobiphenyl by nitrating 4-hydroxybiphenyl using nitric acid, which is characterized in that a mixture of 4-hydroxybiphenyl and glacial acetic acid is heated until the glacial acetic acid boils and the nitric acid or a mixture of nitric acid and glacial acetic acid is then metered into the reflux of the boiling acetic acid.

The process according to the invention provides the desired 4-hydroxy-3-nitrobiphenyl in an improved yield compared to the prior art. In addition, working with large dilutions can surprisingly be avoided. It is of decisive importance for the success of the process according to the invention that the nitric acid is added dropwise either alone or in a mixture with glacial acetic acid to the reflux of the boiling glacial acetic acid, in particular into the gas phase (of the glacial acetic acid reflux). This leads to localized dilution of the nitrating reagent which makes it possible to work with concentrations of the reactant in the solvent which are distinctly higher than in the most similar prior art process. In addition, the reaction product does not need to be purified, as is necessary in the prior art nitrating processes: the product occurs immediately in very high purity which is suitable for any further use.

The process according to the invention initially provides a mixture of 4-hydroxybiphenyl and glacial acetic acid. The amount of 4-hydroxybiphenyl may be 5–50% by weight, preferably 10–30% by weight and more preferably 15–20% by weight, based on the total amount of 4-hydroxybiphenyl and glacial acetic acid.

The mixture of 4-hydroxybiphenyl and glacial acetic acid is then heated until the glacial acetic acid boils. The mixture may be heated by increasing the temperature and optionally by reducing the pressure at the same time. Preference is given to heating with stirring while lowering the pressure at the same time. The mixture of 4-hydroxybiphenyl and glacial acetic acid preferably has a 4-hydroxybiphenyl content of 15–20% by weight and is heated to a temperature of 75–80° C. at a pressure of 200–300 mbar.

Nitric acid or a mixture of glacial acetic acid and nitric acid is added dropwise to the reflux of the boiling glacial acetic acid. The metering rate is dependent upon the boiling temperature, the reflux rate of the glacial acetic acid and the concentration of 4-hydroxybiphenyl in the glacial acetic acid, and may be varied within a wide range.

In general, nitric acid or a mixture of glacial acetic acid and nitric acid are metered into the reflux of the boiling glacial acetic acid at a metering rate of from 0.01 to 1 g/min, preferably from 0.1 to 0.5 g/min and in particular from 0.3 to 0.4 g/min, calculated for 100% nitric acid. The nitric acid may be used in any desired dilution with water, preferably as from 50 to 70% nitric acid and in particular as from 65 to 67% nitric acid. The use of from 65 to 67% nitric acid in particular has proven useful, in particular in a mixture with glacial acetic acid.

When a mixture of glacial acetic acid and nitric acid is added dropwise, from 1:10 to 10:1 mixtures have proven useful. Preference is given to from 7:3 to 3:7 mixtures and in particular a 1:1 mixture of glacial acetic acid and from 65 to 67% nitric acid.

Nitric acid is added dropwise alone or in a mixture with the glacial acetic acid in such an amount that the molar ratio of nitric acid to 4-hydroxybiphenyl used is from 1.2:1 to 0.8:1, preferably from 1.05:1 to 1:1.

After the dropwise addition has ended, stirring of the reaction mixture is continued for a certain time. It has proven useful to continue stirring for from 10 minutes to 1 hour, preferably from 10 minutes to 30 minutes, and in particular about 15 minutes, at a temperature at which the glacial acetic acid continues to boil under the given pressure conditions. The reaction mixture is then added to water.

Neither the continued stirring time, nor the temperature of the reaction mixture when it is added to the water, nor the temperature of the water are essential for the selectivity achieved in the process according to the invention.

In one variant of the process according to the invention, it is also possible to first concentrate the reaction mixture and only then add it to water.

When the reaction mixture is added to the water, the desired 4-hydroxy-3-nitrobiphenyl precipitates and may be removed in a simple manner by filtration, washed once or more than once with water and dried under air.

EXAMPLES

Example 1

A 2 l jacketed flanged beaker equipped with a glass impeller stirrer, thermometer and reflux condenser having an inlet tube is charged with 200 g (1.18 mol) of 4-hydroxybiphenyl and 1000 g of glacial acetic acid. A vacuum of 240 mbar is generated in the apparatus and the mixture heated to 80° C. to vigorous boiling of the glacial acetic acid. Within four hours, a mixture of 116.8 g of glacial acetic acid and 116.8 g of nitric acid (65% by weight, 1.21 mol) is added with stirring at 75–80° C. via a Teflon inlet pipe inserted into the top of the reflux condenser and whose opening is disposed at the height of the last third of the total length of the reflux condenser. After the addition had ended, the mixture was stirred for a further 15 minutes. The reaction mixture is cooled to 40° C. and the apparatus aerated using nitrogen.

The reaction batch is then added within 20 minutes to 3350 g of water at 40° C. Within one and a half hours, the reaction mixture is cooled to 20° C., and the precipitated solid is filtered off and washed twice with 500 g of water each time. The product is then dried at 20° C. overnight in an air stream. 249.6 g of 4-hydroxy-3-nitrobiphenyl are obtained.

The following percentage areas are obtained by means of HPLC, from which a standard is used to determine the accompanying percentages by weight:

|  | % area | % by weight |
|---|---|---|
| 4-hydroxy-3-nitrobiphenyl | 99.3 | 94.2 |
| 4-hydroxybiphenyl | 0.1 | 0.1 |
| 3,5-dinitro-4-hydroxybiphenyl | 0.3 | 0.3 |
| unknown impurity at a retention time of 16.9 min | 0.1 | — |
| unknown impurity at a retention time of 17.8 min | 0.1 | — |

The percentage areas required to make up to a value of 100 are glacial acetic acid.

The yield of 4-hydroxy-3-nitrobiphenyl is accordingly 93% of theory, based on 4-hydroxybiphenyl used.

Example 2
(Comparative Experiment According to the Example in J. Am. Chem. Soc. 47, 1454 (1925) Using a Reactant Concentration of 1.7% by Weight)

A four-necked flask equipped with a reflux condenser, thermometer, stirrer and dropping funnel is initially charged with 4.5 g (0.026 mol) of 4-hydroxybiphenyl in 250 ml of glacial acetic acid. 4.96 g (0.026 mol) of 33% by weight nitric acid is added dropwise with stirring within 90 minutes and the mixture is then heated to 80° C. After 2.5 hours at 80° C., the reaction mixture is poured into 750 g of an ice/water mixture and stirred for a short time. The solid formed is filtered off, washed with cold water and dried over phosphorus pentoxide under reduced pressure.

5.1 g of 4-hydroxy-3-nitrobiphenyl are obtained. This corresponds to a crude yield of 91% of theory.

The following percentage areas are obtained by means of HPLC, from which a standard is used to determine the accompanying percentages by weight:

|  | % area | % by weight |
|---|---|---|
| 4-hydroxy-3-nitrobiphenyl | 97.2 | 91.1 |
| 4-hydroxybiphenyl | 0.5 | 0.6 |
| 3,5-dinitro-4-hydroxybiphenyl | not present | — |
| unknown impurity at a retention time of 16.9 min | 0.4 | — |
| unknown impurity at a retention time of 17.8 min | 1.6 | — |

The percentage areas required to make up to a value of 100 are glacial acetic acid.

The yield of 4-hydroxy-3-nitrobiphenyl is accordingly 100% of theory based on 4-hydroxybiphenyl used.

A melting point of 67.5° C. is determined.

Example 3
(Comparative Experiment According to the Example in J. Am. Chem. Soc. 47, 1454 (1925), but with a Reactant Concentration of 17% by Weight Instead of 1.7% by Weight)

A four-necked flask equipped with a reflux condenser, thermometer, stirrer and dropping funnel is initially charged with 53.8 g (0.316 mol) of 4-hydroxybiphenyl in 250 ml of glacial acetic acid. 60.3 g (0.316 mol) of 33% by weight nitric acid is added dropwise with stirring within 90 minutes and the mixture is then heated to 80° C. After 5 hours at 80° C., the reaction mixture is added to 750 g of an ice/water mixture and stirred for a short time. The solid formed is filtered off, washed with cold water and dried overnight at 20° C. in an air stream.

67.8 g of 4-hydroxy-3-nitrobiphenyl are obtained. This corresponds to a crude yield of 99%.

The following percentage areas are obtained by means of HPLC, from which a standard is used to determine the accompanying percentages by weight:

|  | % area | % by weight |
|---|---|---|
| 4-hydroxy-3-nitrobiphenyl | 95.6 | 79.0 |
| 4-hydroxybiphenyl | 2.3 | 2.2 |
| 3,5-dinitro-4-hydroxybiphenyl | not present | — |
| unknown impurity at a retention time of 16.9 min | 1.1 | — |
| unknown impurity at a retention time of 17.8 min | 0.3 | — |

The percentage areas required to make up to a value of 100 are glacial acetic acid.

The yield of 4-hydroxy-3-nitrobiphenyl is accordingly 79% of theory, based on 4-hydroxybiphenyl used.

What is claimed is:

1. A process for preparing 4-hydroxy-3-nitrobiphenyl by nitrating 4-hydroxybiphenyl using nitric acid, comprising heating a mixture of 4-hydroxybiphenyl and glacial acetic acid until the glacial acetic acid boils and then metering the nitric acid or a mixture of nitric acid and glacial acetic acid into the reflux of the boiling glacial acetic acid.

2. The process as claimed in claim 1, wherein the mixture of 4-hydroxybiphenyl and glacial acetic acid used has a 4-hydroxybiphenyl content of from 5 to 50% by weight.

3. The process as claimed in claim 1, wherein the mixture of 4-hydroxy-biphenyl and glacial acetic acid is heated by increasing the temperature and optionally by reducing the pressure at the same time.

4. The process as claimed in claim 1, wherein the mixture of 4-hydroxy-biphenyl and glacial acetic acid has a 4-hydroxybiphenyl content of from 15 to 20% by weight and the mixture is heated at a pressure of from 200 to 300 mbar to a temperature of from 75 to 8000.

5. The process as claimed in claim 1, wherein the nitric acid is diluted with acid.

6. The process as claimed in claim 1, wherein nitric acid or a mixture of nitric acid and glacial acetic acid is metered into the reflux of the boiling glacial acetic acid at a rate of from 0.01 to 1 g/min, calculated for 100% nitric acid.

7. The process as claimed in claim 1, wherein from 1:10 to 10:1 mixture of glacial acetic acid and from 65 to 67% nitric acid are used.

8. The process as claimed in claim 1, wherein nitric acid is added dropwise alone or in a mixture with the glacial acetic acid in an amount to provide the molar ratio of nitric acid to 4-hydroxybiphenyl is from 1.2:1 to 0.8:1.

9. The process as claimed in claim 1, further comprising filtering off and optionally washing with water, and drying the resulting 4-hydroxy-3-nitrobiphenyl after the reaction mixture is added to water.

10. The process as claimed in claim 2, wherein the mixture of 4-hydroxybiphenyl and glacial acetic acid has a 4-hydroxybiphenyl content of from 10 to 30% by weight.

11. The process as claimed in claim 5, wherein the nitric acid is diluted with water from 50 to 70% nitric acid nitric acid.

12. The process as claimed in claim 11, wherein the nitric acid is diluted with water from 65 to 67% nitric acid.

13. The process as claimed in claim 6, wherein nitric acid or a mixture of nitric acid and glacial acetic acid is metered into the reflux of the boiling glacial acetic acid at a rate of from 0.1 to 0.5 g/min, calculated for 100% nitric acid.

14. The process as claimed in claim 13, wherein nitric acid or a mixture of nitric acid and glacial acetic acid is metered into the reflux of the boiling glacial acetic acid at a rate of from 0.3 to 0.4 g/min, calculated for 100% nitric acid.

15. The process as claimed in claim 7, wherein from 7:3 to 3:7 mixtures of glacial acetic acid and from 65 to 67% nitric acid are used.

16. The process as claimed in claim 15 wherein a 1:1 mixture of glacial acetic acid and from 65 to 67% nitric acid are used.

17. The process as claimed in claim 8, wherein nitric acid is added dropwise alone or in a mixture with the glacial acetic acid in an effective amount to provide the molar ratio of nitric acid to 4-hydroxybiphenyl is from 1.05:1 to 1:1.

* * * * *